United States Patent
Yin et al.

(10) Patent No.: US 10,357,500 B2
(45) Date of Patent: Jul. 23, 2019

(54) NEURO-PROTECTIVE AGENTS AND USES THEREOF

(71) Applicant: Guangzhou Cellprotek Pharmaceutical Co., Ltd., Guangzhou, Guangdong (CN)

(72) Inventors: Wei Yin, Guangzhou (CN); Jiesi Chen, Guangzhou (CN); Guangmei Yan, Guangzhou (CN); Bingzheng Lu, Guangzhou (CN); Wenbo Zhu, Guangzhou (CN); Haiyan Hu, Guangzhou (CN); Pengxin Qiu, Guangzhou (CN); Yijun Huang, Guangzhou (CN); Jingxia Zhang, Guangzhou (CN)

(73) Assignee: Guangzhou Cellprotek Pharmaceutical Co., Ltd., Guangzhou, Guangdong (CN)

( * ) Notice: Subject to any disclaimer, the term of this patent is extended or adjusted under 35 U.S.C. 154(b) by 0 days.

(21) Appl. No.: 15/306,437

(22) PCT Filed: Apr. 14, 2015

(86) PCT No.: PCT/CN2015/076528
§ 371 (c)(1),
(2) Date: Oct. 24, 2016

(87) PCT Pub. No.: WO2015/161747
PCT Pub. Date: Oct. 29, 2015

(65) Prior Publication Data
US 2017/0042909 A1 Feb. 16, 2017

(30) Foreign Application Priority Data
Apr. 25, 2014 (CN) .......................... 2014 1 0170263

(51) Int. Cl.
A61K 31/56 (2006.01)
A61K 31/565 (2006.01)
A61K 31/575 (2006.01)

(52) U.S. Cl.
CPC ............ *A61K 31/56* (2013.01); *A61K 31/565* (2013.01); *A61K 31/575* (2013.01)

(58) Field of Classification Search
CPC ..... A61K 31/56; A61K 31/565; A61K 31/575
See application file for complete search history.

(56) References Cited

U.S. PATENT DOCUMENTS 5,856,331 A * 1/1999 Bursten ............... A61K 31/52
514/183
2013/0157993 A1 6/2013 Yan et al.

FOREIGN PATENT DOCUMENTS

| CN | 101683348 | * | 3/2010 |
| CN | 101884638 | * | 11/2010 |
| CN | 102180928 | | 9/2011 |
| EP | 2591785 | | 1/2017 |
| WO | WO 2012/003802 | | 1/2012 |

OTHER PUBLICATIONS

Chen et al., "A synthetic steroid 5alpha-androst-3beta,5,6beta-triol blocks hypoxia/reoxygenation-induced neuronal injuries via protection of mitochondrial function", Steroids, vol. 78(10), pp. 996-1002, 2013.*
International Search Report and Written Opinion of PCT/CN2015/076528 dated Jul. 9, 2015 with English translation (15 pages).
Full Examination Report for AU Patent Application No. 2015251359 dated Apr. 21, 2017 (3 pages).
Basnyat, "High altitude cerebral and pulmonary edema", Travel Medicine and Infecftious Disease (2005) vol. 3, pp. 199-211.
First Office Action for CN 20140170263.7 dated Apr. 28, 2017 (6 pages), Eng. translation needed.
Extended European Search Report for EP 15783742.8 dated Sep. 18, 2017 (7 pages).
Felszeghy et al., Dexamethasone Downregulates chemokine receptor CXCR4 and Exerts Neuroprotection against Hypoxia/Ischemia-Induced Brain Injury in Neonatal Rats, :Nkueroimmunomodulation (2004) vol. 11, pp. 404-413.
Levine et al., "Dexamethasone in the treatment of acute mountain sickness," New England Journal of Medicine, (1989) vol. 321, No. 25, pp. 1707-1713.
Li et al, "Research Progress in Mechanisms andPathophysiology of Acute Mountain Sickness", Medical Recapitulate, Apr. 2013, vol. 19, No. 8, pp. 1352-1354, Abstract only.
Netzer et al., "Hypoxia-Related Altitude Ilnesses", Journal of Travel Medicine, (2013) vol. 20, pp. 247-255.
Gonzalez-Rodriguez et al., "Fetal Hypoxia Increases Vulnerability of Hypoxic-Ischemic Brain Injury in Neonatal Rats: Role of Glucocorticoid Receptors", Neurobio. Dis. (2014) vol. 65, pp. 172-179.
Pang et al., Dexamethasone and betamethasone protect against LPS-induced brain damage in the neonatal rats,: Pediatr Res. (2012) vol. 71, No. 5, pp. 552-558.

(Continued)

Primary Examiner — Barbara P Badio
(74) Attorney, Agent, or Firm — Sheppard Mullin Richter & Hampton LLP

(57) ABSTRACT

Use of 5α-androstane-3β,5,6β-triol and analogs thereof in the preparation of a drug for the prophylaxis or treatment of an altitude sickness caused by hypobaric hypoxia is provided, so as to provide a new drug for the prophylaxis or treatment of an altitude sickness. Researches revealed that 5α-androstane-3β,5,6β-triol treatment can effectively reduce vasogenic edema of brain tissue of *Macaca fascicularis* caused by hypobaric hypoxia, reduce the increased cerebral water content, and protect from neuronal vacuolar degeneration caused by hypobaric hypoxia, therefore it can improve neurological dysfunctions caused by hypobaric hypoxia and is useful in prophylaxis or treatment of an altitude sickness.

6 Claims, 1 Drawing Sheet

(56) References Cited

OTHER PUBLICATIONS

Written Opinion of Singapore Patent Application No. 11201608829S dated Mar. 23, 2017 (6 pages).
Wright et al., "High hopes at high altitudes: pharmacotherapy for acute mountain sickness and high-altitude cerebral and pulmonary oedema," Expert Opinion, Pharmacotherpy (2008) vol. 9 No. 1, pp. 119-127.
Yang et al., "Acetazolamide impairs fear memory consolidation in rodents," Neuropharmacology 67 (2013), pp. 412-418.
Zafren, "Does Ibuprofen Prevent Acute Mountain Sickness", Wilderness & Environmental Medicine, (2012) vol. 23, pp. 297-299.
Zou, "Research Progress of Acetazolamide in Controlling Highland Disease", People's Military Surgeon, vol. 58, No. 4, Apr. 2015, pp. 450-451, Eng. translation needed.
First Office Action of Russian Patent Application No. RU 2016141462/15 dated Jan. 31, 2018 (pp. 1-10).
Second Office Action of Russian Patent Application No. RU 2016141462/15 dated May 28, 2018 (pp. 14-23).

* cited by examiner

NEURO-PROTECTIVE AGENTS AND USES THEREOF

CROSS-REFERENCE TO RELATED APPLICATIONS

This application is a U.S. National Stage Application under 35 U.S.C. § 371 of International Application No. PCT/CN2015/076528, filed Apr. 14, 2015, which application claims priority to Chinese Patent Application No. 201410170263.7 filed Apr. 25, 2014, the content of each of which is hereby incorporated by reference in its entirety.

TECHNICAL FIELD

The present invention relates to a novel pharmaceutical usage of compound 5α-androstane-3β,5,6β-triol and analogs thereof.

BACKGROUND

Atmospheric pressure and oxygen partial pressure decrease as the altitude rises. Low level of partial pressure of oxygen in inspired air results in the decrease of arterial blood oxygen partial pressure, decrease of oxygen content, and insufficient oxygen delivery to tissues. This condition, which is called hypobaric hypoxia (HH), mainly occurs in high altitude areas, and thus is also referred to as high altitude hypoxia.

Acute Hypobaric Hypoxia occurs when one reaches an area with an altitude of over 2500 meters. If one can not acclimate such an environmental change, he or she may suffer successively from High-Altitude Headache (HAH) and Acute Mountain Sickness (AMS). Moreover, AMS may further develop into High-Altitude Cerebral Edema (HACE) and High-Altitude Pulmonary Edema (HAPE). A large number of reports have showed that clinical features caused by altitude sicknesses include neurological symptoms such as headache, polylogia, insomnia, gait disturbance, impaired mental ability, somnolence, mental numbness and ataxia.

Current therapeutics for altitude sicknesses majorly was focus on the improvement of oxygen delivery, and cytokines or inflammatory responses. A representative drug of the former is acetazolamide, a carbonic anhydrase inhibitor. Exemplary drugs of the latter include glucocorticoids and some antioxidants (Wright A, Brearey S, Imray C. High hopes at high altitudes: pharmacotherapy for acute mountain sickness and high-altitude cerebral and pulmonary oedema. *Expert Opin Pharmacother* 2008 January; 9(1):119-27). There has been no report regarding use of a neuro-protective agent for treating altitude sicknesses.

Chinese Patent No. ZL 2010 1 0224173.3 to Sun Yat-Sen University disclosed a newly discovered neuro-protective agent, 5α-androstane-3β,5,6β-triol, having a formula of:

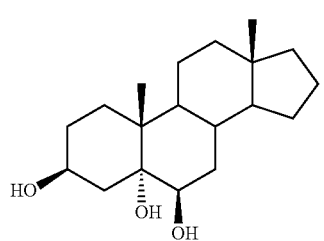

The present inventors surprisingly found that 5α-androstane-3β,5,6β-triol and its analogs could significantly improve the neurological scores in individuals with hypobaric hypoxia treatment and protect the brain from pathological damage caused by hypobaric hypoxia. These compounds are prospective for use in prophylaxis or treatment of altitude sicknesses caused by hypobaric hypoxia.

SUMMARY

An objective of the present invention is to provide the use of a 3β,5α,6β-trihydroxyl steroid compound having formula A or a pharmaceutically acceptable salt thereof in the preparation of a pharmaceutical composition for the prophylaxis or treatment of an altitude sickness caused by hypobaric hypoxia:

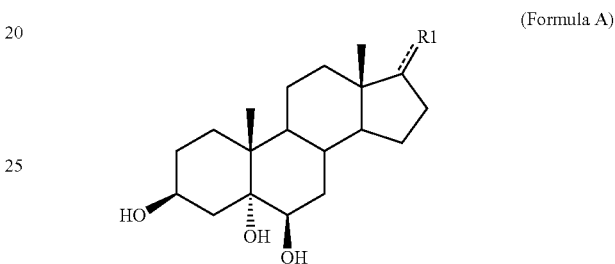

(Formula A)

wherein R1 is H or a linear or branched alkyl or terminal alkenyl having 1 to 5 carbon atoms.

In one embodiment, R1 is H, and the compound is 5α-androstane-3β,5,6β-triol (also abbreviated as YC-6 herein).

In one embodiment, the altitude sickness is an acute altitude sickness caused by high-altitude acute hypobaric hypoxia.

In another embodiment, the altitude sickness is high-altitude cerebral edema and particularly high-altitude cerebral angioedema.

In another embodiment, the altitude sickness is neuron damage, specifically neuron degeneration damage including neuron damages caused by high-altitude acute hypobaric hypoxia and high-altitude chronic hypobaric hypoxia.

In another embodiment, the pharmaceutical composition further comprises an additional component for the prophylaxis or treatment of an altitude sickness caused by hypobaric hypoxia, such as carbonic anhydrase inhibitors (e.g., acetazolamide), glucocorticoids or antioxidants.

In the present invention, a non-human primate hypobaric hypoxia model has demonstrated that 5α-androstane-3β,5,6β-triol significantly improves the neurological scores in hypobaric hypoxia treatment groups and protects the brain from pathological damage caused by hypobaric hypoxia, indicating prophylaxis or treatment effects against high-altitude cerebral edema (AMS) and high-altitude pulmonary edema (HACE).

Further researches reveal that the increase of cerebral water content caused by hypobaric hypoxia is effectively blocked by 5α-androstane-3β,5,6β-triol. Vasogenic brain edema and neuronal vacuolar degeneration caused by hypobaric hypoxia is reduced by 5α-androstane-3β,5,6β-triol by pathologic analysis with electron microscopy and HE staining.

In another embodiment, R1 is —CH(CH$_3$)(CH$_2$)$_3$CH(CH$_3$)$_2$, so the compound is cholestane-3β,5α,6β-triol (Compound I). Chinese Patent No. ZL 200810198703.4 to Sun Yat-sen University disclosed that Compound I was also neuron-protective. Similarly, we found the compound could also effectively reduce vasogenic brain edema and neuronal vacuolar degeneration caused by hypobaric hypoxia. The Compound I has the formula of:

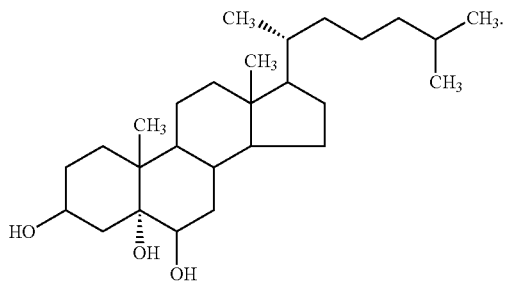 [SMILES: CC(C)CCC[C@@H](C)C1CCC2C3CC(O)[C@@]4(O)CC(O)CCC4(C)C3CCC21C]

Chinese Patent No. ZL 201110061235.8 disclosed the neuron protection effects of other compounds within the formula A. We also found that these compounds were effective in reducing vasogenic brain edema caused by hypobaric hypoxia, blocking elevation of brain water content, and protecting from neuronal vacuolar degeneration caused by hypobaric hypoxia.

In the embodiments where R1 is —CHCH$_2$CH$_3$, —CH(CH$_3$)$_2$ or —CH(CH$_2$)$_3$CH$_3$, the compound is 17-propylidene-androstane-3β,5α,6β-triol (Compound II), 17-isopropyl-androstane-3β,5α,6β-triol (Compound III), or 17-butyl-androstane-3β,5α,6β-triol (Compound IV), respectively.

Another objective of the present invention is to provide a method for the prophylaxis or treatment of an altitude sickness caused by hypobaric hypoxia, comprising administering to a subject in need thereof an effective amount of a 3β,5α,6β-trihydroxyl steroid compound having formula A or a pharmaceutically acceptable salt thereof:

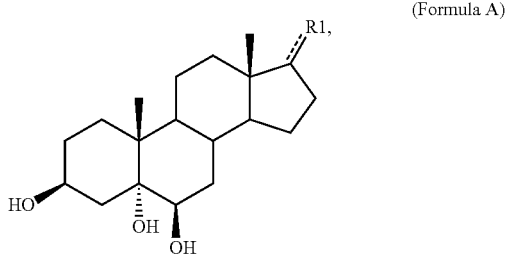

(Formula A)

wherein R1 is H or a linear or branched alkyl or terminal alkenyl having 1 to 5 carbon atoms.

In one embodiment, R1 is H, and the compound is 5α-androstane-3β,5,6β-triol (also abbreviated as YC-6 herein). In another embodiment, R1 is —CH(CH$_3$)(CH$_2$)$_3$CH(CH$_3$)$_2$, the compound is thus cholestane-3β,5α,6β-triol (Compound I). In other embodiments, R1 is —CHCH$_2$CH$_3$, —CH(CH$_3$)$_2$ or —CH(CH$_2$)$_3$CH$_3$, the compound is 17-propylidene-androstane-3β,5α,6β-triol (Compound II), 17-isopropyl-androstane-3β,5α,6β-triol (Compound III), or 17-butyl-androstane-3β,5α,6β-triol (Compound IV), respectively.

In embodiments of the invention, the altitude sickness is selected from a group consisting of an acute altitude sickness, high-altitude cerebral edema, neuron damage caused by acute hypobaric hypoxia and neuron damage caused by chronic hypobaric hypoxia.

In embodiments of the invention, the subject is mammalian, for example a human being.

5α-androstane-3β,5,6β-triol and its analogs structurally belong to 3β,5α,6β-trihydroxyl steroids and are effective to protect neurons. The present inventors found that those compounds were effective in the prophylaxis or treatment of an altitude sickness caused by hypobaric hypoxia.

DETAILED DESCRIPTION OF THE INVENTION

Figure 1:
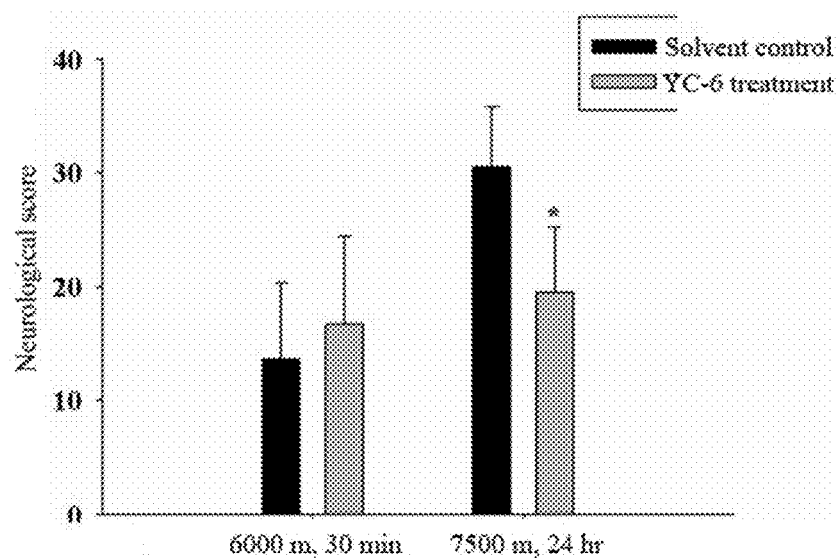
FIG. 1: Neurological score was significantly improved in *Macaca fascicularis* by 5α-androstane-3β,5,6β-triol after acute hypobaric hypoxia exposure. *$P<0.05$, 5α-androstane-3β,5,6β-triol treatment group vs. solvent control.

The present invention will be described in more detail in reference to specific examples. It should be understood that the scope of the invention will not be limited by the examples.

Verification of the New Usage of 5α-Androstane-3β,5,6β-triol

1. Animals 17 healthy male *Macaca fascicularis*, 6 to 6.5 years-old, weighted 6.8-7.5 kg, were used. The use of laboratory animals is approved by Committee of laboratory animal management and use and experimental animal ethics committee. The experiment scheme complies with rules concerning animal protection, animal welfare and ethical principles. The 17 *Macaca fascicularis* were grouped randomly into 3 groups (Table 1).

TABLE 1

Animal Grouping

| Group | Treatment |
|---|---|
| 1 (n = 6) | Plain control: normobaric normoxia |
| 2 (n = 5) | Solvent control: glucose saline (simulating acute high-altitude hypoxia at 7,500 m altitude) |
| 3 (n = 6) | 5α-androstane-3β,5,6β-triol treatment: 10 mg/kg 5α-androstane-3β,5,6β-triol (simulating acute high-altitude hypoxia at 7,500 m altitude) |

2. Principle Apparatus and Parameters

The low pressure chamber group is a platform used to simulate low temperature and low pressure plateau environment. The system can be manipulated to simulate a low pressure environment having any altitude below 10000 meters and any temperature above −30° C. The ascending velocity: 3 m/second (0 to 6000 m); descending velocity: 2 m/second (6000 m to 7500 m); constant temperature: 22° C.; average air flow velocity: 150 m³/h.

3. Modeling of Acute Hypobaric Hypoxia in *Macaca fascicularis* and Drug Administering (1) An altitude of 7,500 meters was simulated by manipulation of the low-pressure chamber to cause acute hypoxia in *Macaca fascicularis*.

The *Macaca fascicularis* raised in the laboratory animal housing were labeled and transferred to the low-pressure chamber. The *Macaca fascicularis* was fed for 1 more day in the chamber in order to make them adapt to the experimental environment. The pressure in the low-pressure chamber was adjusted to simulate altitudes of 3,000, 4,500, and 6,000 meters, staying at each altitude for 30 minutes, followed by simulation of an altitude of 7,000 meters for 24 hours. The animals were then treated with drugs individually at pre-determined doses. After treatment at 7,500 meters for 48 hours, the altitude was decreased to 6,000 meters at a velocity of 3 m/s. The animals were subject to ketamine anesthesia, sacrificed, dissected and subject to sampling. The samples were fixed. Animals grouped in plain controls were raised in an animal housing at an altitude of 350 m before assessment and sacrifice.

(2) The animals in 5α-androstane-3β,5,6β-triol treatment group were administered through intravenous injection 10 mL of 5α-androstane-3β,5,6β-triol solution in glucose saline at a dosage of 10 mg/kg before simulation, after 30 min at 3,000 meters, and after 30 min at 4,500 meters, respectively. The animals in solvent control group were given 10 mL of glucose saline through intravenous injection.

(3) The animals in 5α-androstane-3β,5,6β-triol treatment group were administered by skeletal muscle injection at 5 different points with 5α-androstane-3β,5,6β-triol sustained-release formulation at a dosage of 30 mg/kg after 30 min at 6,000 meters. Acute plateau hypoxia models were administered 10 mL of glucose saline through intravenous injection.

(4) The animals in 5α-androstane-3β,5,6β-triol treatment group were administered through intravenous injection 10 mL of 5α-androstane-3β,5,6β-triol injection in glucose saline at a dosage of 10 mg/kg after 24 hours at 7,500 meters, and further by skeletal muscle injection at 5 different points with 5α-androstane-3β,5,6β-triol sustained-release formulation at a dosage of 30 mg/kg. Acute plateau hypoxia models were administered 10 mL of glucose saline through intravenous injection.

4. Evaluation Index 4.1 Neurological Scores

Animals were stayed at simulated altitude of 7,500 meters for 24 hours before descending to 6,000 meters at a speed of 3 m/s. The neurological scores were evaluated and recorded according to a reported method (Zhu et al, An improved method of neurological score for non-human primates, *Chinese Journal of Comparative Medicine*, 2011, 21 (9): 58-62). The neurological score was evaluated and recorded by two trained observers who were neither aware of the grouping nor involved in the drug administering. The score was obtained as a mean value.

4.2 Measurement of Cerebral Water Content of Left Hemisphere

Cerebral water content was measured according to a reported method (Patir H, Sarada S K, Singh S, Mathew T, Singh B, Bansal A. Quercetin as a prophylactic measure against high altitude cerebral edema. *Free Radic Biol Med* 2012 Aug. 15; 53(4):659-68). Animals stayed at the simulated altitude of 7,500 meters for 48 hours in the low-pressure chamber and animals of the plain control were narcotized and sacrificed by technicians who were neither aware of the grouping nor involved in the drug administering. Brains of the animals were rapidly taken out and the wet weights of the left hemispheres were measured. The left hemispheres were then placed in a drying oven at 60° C., and were measured their weights daily at a fixed time until no weight change was observed. The end weights were recoded. The cerebral water content=(wet weight of the left hemisphere−dry weight of the left hemisphere)/wet weight of the left hemisphere×100%.

4.3 Transmission Electron Microscopy of the Cortical Tissue of the Frontal Lobe

The cortical tissues of the frontal lobes of the animals were taken out and cut to provide brain pieces of 1 mm³, which were fixed in a stationary liquid of 2.5% glutaraldehyde to prepare ultrathin sections. The morphology of neurons and the structure of blood vessels were observed by transmission electron microscopy.

4.4 HE Staining of the Cortical Tissue of the Frontal Lobe

The cortical tissues of the frontal lobes of the animals were taken out and cut to provide blocks of 1 cm³, which were fixed in 4% paraformaldehyde. Paraffin embedding, sectioning, and haematoxylin-eosin staining were then conducted according to conventional HE staining procedures followed by observation under microscope.

4.5 Statistics

The results were indicated as mean±standard deviation, and statistically analyzed by software SigmaPlot. P≤0.05 indicates statistical significance.

The results demonstrated that neurological function of the *Macaca fascicularis* in a hypobaric hypoxia environment was significantly protected by 5α-androstane-3β3,5,6β-triol. Animals stayed at the simulated altitude of 6,000 meters for 30 minutes in the low-pressure chamber significantly reduced their actions and activities, and also their reactions to intimidating and stimulus. After ascending the simulated altitude to 7,500 meters for 24 hours, the *Macaca fascicularis* in the solvent control showed significant consciousness inhibition, greatly reduced actions and activities, and dysfunction in their moving system and sensing system, with a neurological score of 31.6±4.2. By contrast, the neurological score of the animals in the 5α-androstane-3β3,5,6β-triol treatment group was 20.5±5.7 (P<0.01), indicating that their neurological function was effectively protected (FIG. 1).

Increased cerebral water content of the *Macaca fascicularis* in a hypobaric hypoxia environment was significantly reduced by 5α-androstane-3β3,5,6β-triol. As showed by the calculated cerebral water content, the cerebral water content of the *Macaca fascicularis* in the plain control was 76.155%. By contrast, after treatment in the simulated altitude of 7,500 meters for 48 hours in the low-pressure chamber, the cerebral water content of the *Macaca fascicularis* in the solvent control was increased to 76.714% (P<0.05). In situation where 5α-androstane-3β3,5,6β-triol was administered before ascending to 7,500 meters, and 5α-androstane-3β3,5,6β-triol was administered again after maintaining at 7,500 meters for 24 hours, the cerebral water content of the *Macaca fascicularis* was decreased to 76.283% (P<0.05), demonstrating that administration of 5α-androstane-3β,5, 6β-triol can inhibit the increase of cerebral water content of the *Macaca fascicularis* in an acute hypobaric hypoxia environment (Table 2).

TABLE 2

Influence of 5α-androstane-3β,5,6β-triol on the cerebral water content of the *Macaca fascicularis* in a hypobaric hypoxia environment

| Group | Cerebral Water Content (%) |
|---|---|
| Plain control | 76.155 ± 0.302 |
| Solvent control | 76.714 ± 0.262 # |
| 5α-androstane-3β,5,6β-triol treatment | 76.283 ± 0.235 * |

\#: Compared with plain control, P < 0.05;
\*: Compared with solvent control, P < 0.05.

Figure 2:
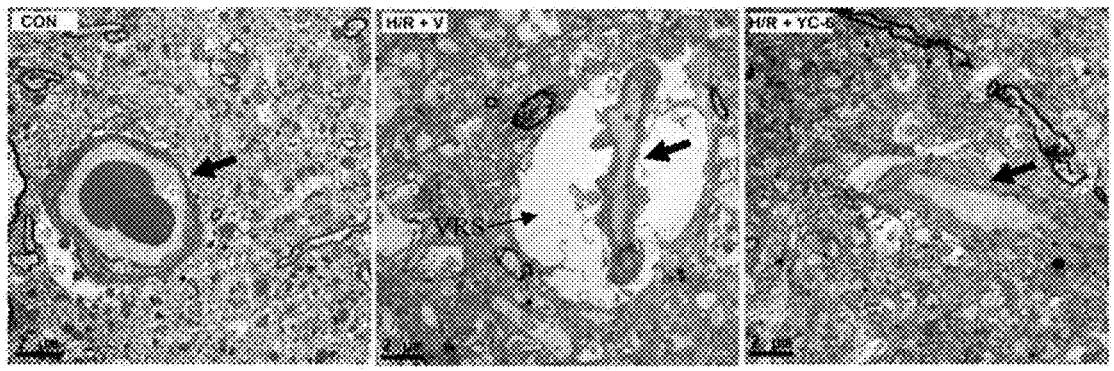
FIG. 2: Vasogenic edema of cerebral cortex tissue in *Macaca fascicularis* caused by acute hypobaric hypoxia was reduced by 5α-androstane-3β,5,6β-triol (transmission electron microscope, 3900×). Con: plain control; H/R+V: solvent control; H/R+YC-6: 5α-androstane-3β,5,6β-triol treatment group. Thick arrows indicate capillary vessels in the cortical tissue of the frontal lobe and thin arrows indicate the Virchow-Robin spaces (VRS).

Vasogenic edema caused by hypobaric hypoxia was reduced by 5α-androstane-3β,5,6β-triol. As observed under transmission electron microscope, the capillary vessels in cortical tissue of frontal lobe of the *Macaca fascicularis* in the solvent control showed significantly broadened Virchow-Robin space (VRS) at its outside as compared with the plain control, indicating severe vasogenic edema leakage. However, the brain tissue of the *Macaca fascicularis* treated by 5α-androstane-3β,5,6β-triol showed Virchow-Robin space that tending to be normal, indicating that no significant vasogenic edema occurred (FIG. 2).

Figure 3:
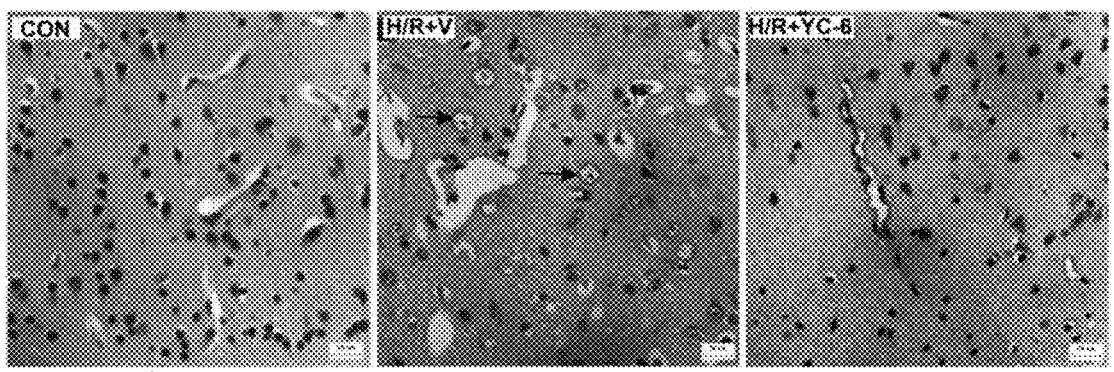
FIG. 3: Degeneration of neurons of cerebral cortex in *Macaca fascicularis* caused by acute hypobaric hypoxia was reduced by 5α-androstane-3β,5,6β-triol (HE staining, 400×). Con: plain control; H/R+V: solvent control; H/R+YC-6: 5α-androstane-3β,5,6β-triol treatment group. Arrows indicate neurons undergone degeneration.

Neuronal vacuolar degeneration caused by hypobaric hypoxia was reduced by 5α-androstane-3β,5,6β-triol. As observed after HE staining, the cortical tissue of the frontal lobe in the solvent control showed significantly loosened structure, with edematous fluid appearing around the vessel and oppressing the lumen, and also showed partly neuronal degeneration with shrinking somas and pyknotic nucleus, indicating a vacuolar degeneration (indicated by arrows). The 5α-androstane-3β,5,6β-triol treatment group showed no significant vasogenic edema, and reduced neuronal vacuolar degeneration similar to the plain control, demonstrating that 5α-androstane-3β,5,6β-triol protected the neurons in the hypobaric hypoxia environment (FIG. 3).

Pharmaceutical Composition

Injections and sustained-release suspensions of 5α-androstane-3β3,5,6β-triol were used in the embodiments. However, preparations for prophylaxis or treatment of altitude sicknesses caused by hypobaric hypoxia include, but are not limited to, injections, sustained-release suspensions, oral capsules, suppositories, subdermal implants, and attachable plasters.

(1) Preparation of 5α-Androstane-3β3,5,6β-triol (YC-6) Injection

Preparation of 20% HP-β-CD solution: 20.0 g of HP-β-CD was added with 80 mL of normal saline, and then stirred to dissolve. Normal saline was added to provide a 100 ml solution. The solution was subject to refined filtration by 0.22 µm microporous membrane and then separately filled in 15 mL centrifuge tubes which were then sealed and stored at 4° C.

Preparation of 2 mg/ml YC-6 solution: 6.0 g of HP-β-CD was added with 24 mL of deionized water, and then stirred to dissolve. 0.060 g of YC-6 was added to the above HP-β-CD solution, which was then stirred to dissolve. 0.270 g of sodium chloride was added and then stirred to dissolve. Deionized water was added to provide a 30 mL solution. The solution was subject to refined filtration by 0.22 µm microporous membrane and then separately filled in 1.5 mL Eppendorf tubes which were then sealed and stored at 4° C. for later use. Administration dosage in use for the solution is 10 ml/kg, which is equivalent to 20 mg/kg dosage for the drug.

(2) Preparation of 5α-Androstane-3β3,5,6β-triol (YC-6) Sustained-Release Suspensions The sustained-release suspensions were prepared by: YC-6 12.5 g, glycerin 30 mL, HP-β-CD 50 g, CMC-Na 0.48 g, which were added with water for injection to be 250 mL.

Preparation of 0.8% CMC-Na solution: 0.8 g of CMC-Na was added into 90 mL of 90° C. water in several times, with stirring until completely added and dissolved. The solution was allowed to be cooled to room temperature, and then added with water to provide a 100 mL solution. The solution was then stirred and subject to centrifugation at 3000 r/min for 15 min. The supernatant was separated for later use.

Preparation of 40% HP-β-CD solution: 80 g of HP-β-CD was added into about 100 mL of water, which was then stirred and dissolved. Water was added to provide a 200 mL solution for later use.

About 12.5 g of YC-6 was placed in a container to be grinded. 30 mL of glycerin was added and the mixer was grinded to provide a milk white lubricant as a paste. 125 mL of 40% HP-β-CD aqueous solution was gradually added while being grinded. 60 mL of 0.8% CMC-Na was added while being grinded to avoid generation of too many bubbles. The reaction was transferred to a volumetric flask which was filled with water for injection to provide a 250 mL solution followed by being shaken.

Verification of the New Usage of Analogs of 5α-Androstane-3β,5,6β-triol

The above experiments for the model of *Macaca fascicularis* in acute hypobaric hypoxia were repeated under the same conditions except that the YC-6 was replaced by the above compounds I, II, III and IV. As showed by the results, similarly, the neurological function of the *Macaca fascicularis* treated by compounds II, III and IV was effectively protected, with inhibited increase of the cerebral water content, and no significant angioedema. It can be seen that analogs of 5α-androstane-3β3,5,6β-triol, especially compound I and the compound having formula A, especially compounds II, III and IV, are useful in prophylaxis or treatment of altitude sicknesses caused by hypobaric hypoxia.

It should be understood that the above examples are merely preferable embodiments of the present invention, and the scope of the invention will not be limited by the examples. Variations or modifications can be made by a skilled person in the art based on the disclosure of the present invention without departing from the scope of the claims.

What is claimed is:

1. A method for treatment of high-altitude cerebral edema caused by hypobaric hypoxia, comprising administering to a subject that suffers from high-altitude cerebral edema caused by hypobaric hypoxia an effective amount of a 3β,5α,6β-trihydroxyl steroid compound having the formula of:

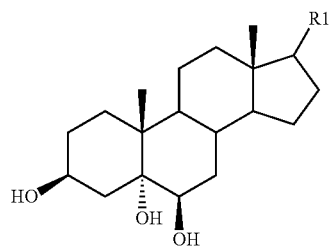

or a pharmaceutically acceptable salt thereof, wherein R1 is H, a linear or branched alkyl having 1 to 5 carbon atoms, a terminal alkenyl having 1 to 5 carbon atoms, or —CH(CH$_3$)(CH$_2$)$_3$CH(CH$_3$)$_2$.

2. The method of claim 1, wherein the subject is mammalian.

3. The method of claim 2, wherein the mammalian is a human being.

4. The method of claim 1, wherein the high-altitude cerebral edema is vasogenic edema.

5. The method of claim 1, wherein R1 is H.

6. The method of claim 1, wherein R1 is selected from a group consisting of —CHCH$_2$CH$_3$, —CH(CH$_3$)$_2$, —CH(CH$_2$)$_3$CH$_3$ and —CH(CH$_3$)(CH$_2$)$_3$CH(CH$_3$)$_2$.

* * * * *